(12) United States Patent
Lopatin et al.

(10) Patent No.: US 8,261,615 B2
(45) Date of Patent: Sep. 11, 2012

(54) APPARATUS FOR DETERMINING AND/OR MONITORING A PROCESS VARIABLE OF A MEDIUM

(75) Inventors: Sergej Lopatin, Lörrach (DE); Helmut Pfeiffer, Steinen (DE); Sascha D'Angelico, Rümmingen (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 321 days.

(21) Appl. No.: 12/448,948

(22) PCT Filed: Dec. 20, 2007

(86) PCT No.: PCT/EP2007/064331
§ 371 (c)(1),
(2), (4) Date: Jan. 4, 2010

(87) PCT Pub. No.: WO2008/086936
PCT Pub. Date: Jul. 24, 2008

(65) Prior Publication Data
US 2010/0154546 A1 Jun. 24, 2010

(30) Foreign Application Priority Data

Jan. 16, 2007 (DE) .......................... 10 2007 003 103
Nov. 26, 2007 (DE) .......................... 10 2007 057 124

(51) Int. Cl.
*G01N 29/00* (2006.01)
(52) U.S. Cl. ........................................... 73/649; 73/632
(58) Field of Classification Search .................... 73/649, 73/290 V, 861.27, 291, 584, 632
See application file for complete search history.

(56) References Cited

U.S. PATENT DOCUMENTS

| 4,114,423 | A  |   | 9/1978  | Wenger |
| 6,711,942 | B2 | * | 3/2004  | Getman et al. ............... 73/54.25 |
| 6,845,663 | B2 | * | 1/2005  | Lopatin et al. .............. 73/290 V |
| 7,210,349 | B2 | * | 5/2007  | Kurihara et al. ........... 73/504.12 |
| 7,436,100 | B2 | * | 10/2008 | D'Angelico et al. ......... 310/319 |
| 7,530,268 | B2 | * | 5/2009  | Lopatin et al. .............. 73/290 V |
| 7,714,480 | B2 | * | 5/2010  | Ohnishi et al. ................ 310/324 |

FOREIGN PATENT DOCUMENTS

| CH | 681 113 A5     | 1/1993  |
| DE | 689 01 828 T2  | 12/1992 |
| JP | 2005 151663 A  | 6/2005  |
| WO | WO 03/002952 A1 | 1/2003 |
| WO | WO 2004/036191 A1 | 4/2004 |

\* cited by examiner

*Primary Examiner* — J M Saint Surin
(74) *Attorney, Agent, or Firm* — Bacon & Thomas, PLLC (57) ABSTRACT

An apparatus for determining and/or monitoring at least one process variable of a medium, including: at least one mechanically oscillatable membrane, which has a plurality of natural eigenmodes; and at least one driving/receiving unit, which excites the membrane to execute mechanical oscillations and/or which receives mechanical oscillations from the membrane. The driving/receiving unit and the membrane are embodied and matched to one another in such a manner, that the membrane executes only mechanical oscillations, which correspond to modes, which lie above the fundamental mode of the membrane.

32 Claims, 4 Drawing Sheets

APPARATUS FOR DETERMINING AND/OR MONITORING A PROCESS VARIABLE OF A MEDIUM

TECHNICAL FIELD

The invention relates to an apparatus for determining and/or monitoring at least one process variable of a medium. The apparatus includes: at least one, mechanically oscillatable membrane, or diaphragm, which has a plurality of natural eigenmodes; and at least one driving/receiving unit, which excites the membrane to execute mechanical oscillations and/or which receives mechanical oscillations from the membrane. The process variable is, for example, the fill level, the density or the viscosity of the medium, which is, for example, a liquid or a bulk good. The medium is located, preferably, in a container.

BACKGROUND DISCUSSION

Known in the state of the art for determining fill level and other process variables of a medium are so called oscillatory forks and single-rods. Used, in such case, is the fact that the characterizing variables (oscillation amplitude, resonance frequency, phase as a function of frequency) of the oscillations of the oscillatable unit are a function of contact with the medium and also a function of properties of the medium. Thus, for example, the frequency or the amplitude of the oscillations decreases, when the medium reaches, and at least partially covers, the oscillatable unit. Therefore, from the reduction of the oscillation frequency or the amplitude, it can be deduced that the medium has reached a fill level dependent on the embodiment and the mounting position of the apparatus. Furthermore, the oscillation frequency is also dependent, for example, on the viscosity and the density of the medium. In the case of embodiment in the form of an oscillatory fork, such measuring devices include at least two spades, or fork tines, which are mounted on a membrane and which oscillate with counter, or opposite, phase, relative to one another. This measuring principle is universally applicable for liquids and bulk goods. Through the spades, it is, however, not possible to provide a flush-mounted measuring device, since such measuring devices always have at least two spades, which register the medium.

Important in the case of mechanically oscillatable systems is, in general, that no oscillatory energy is lost, e.g. via coupling with the container. An energy loss is usually connected with a loss of applicability, or with defective measurements, or, in the application as switch, with erroneous switchings. At the same time, the energy loss can seldom be compensated by a higher driving power, since the described measuring devices, which, most often, are applied as switches, are usually operated with a small, and limited, energy supply.

For as broadly applicable measurements as possible, it is, furthermore, advantageous, when the effective mass of the mechanically oscillatable unit is as small as possible and the effective area, which comes in contact with the medium, is as large as possible. Against these considerations, however, is the problem, that the oscillatable unit is, preferably, introduced into the medium-containing container through bores which are as small as possible.

So-called membrane oscillators, or sensors, which work with the fundamental bending mode of the membrane, find only very limited applicability in measurements technology, since, in such case, there are always mechanical couplings of the membrane with the process connection. Therefore, such measuring devices can only be used in very limited cases for liquids and bulk goods. Advantageous, however, is that such vibratory limit switches, because they involve only a single membrane, enable a flushly mounting construction. This facilitates cleaning of the container/tank and brings advantages for process equipment in the foods industry, as well as in the production of chemicals and pharmaceuticals, etc.

SUMMARY OF THE INVENTION

An object of the invention, therefore, is to provide a vibratory measuring device, whose oscillatable unit is, as much as possible, well mechanically decoupled and which reliably detects process variables of the medium, even in the case of installation in small connections.

For achieving the object, the invention resides in feature that the driving/receiving unit and the membrane are embodied and matched to one another in such a manner, that the membrane only executes mechanical oscillations, which correspond to modes, which lie above the fundamental mode of the membrane. Or, in other words: The membrane is excited to harmonic oscillations, which lie above the fundamental wave, or the fundamental mode, of the membrane.

In the invention, in an embodiment, especially counter-phase, or opposite phase, oscillation modes of the membrane, especially a circularly shaped membrane, are excited. Depending on geometric dimensions, the oscillation frequency lies, on occasion, above 20 kHz, such as, for example, in the case of a membrane of 1 inch diameter and about 1 mm thickness. The oscillation frequency depends, in such case, on the membrane thickness and the membrane diameter, as well as on the applied material. The medium is located, preferably, in a container, into whose wall the membrane can be flushly mounted.

An embodiment of the invention includes, that the driving/receiving unit and the membrane are embodied and/or arranged relative to one another in such a manner, that the occurrence of mechanical oscillations of the membrane, which correspond to the fundamental mode of the membrane, is essentially prevented. In an embodiment, the driving/receiving unit is embodied and connected with the membrane in such a manner, that the driving/receiving unit can excite no fundamental mode of the membrane. In an additional embodiment, the membrane is embodied in such a manner, that oscillations in the fundamental mode are prevented.

An embodiment of the invention provides that the driving/receiving unit excites essentially only the membrane to executes oscillations. For the decoupling, it can occur, that at least one part of the mounting of the membrane experiences forces and moments. The mounting is, in such case, however, a component of the measuring device, so that the decoupling occurs via the measuring device and at least no forces or moments are transferred onto the container.

An embodiment of the invention includes, that the driving/receiving unit and the membrane are embodied and matched to one another in such a manner, that the membrane executes mechanical oscillations, such that 2*n sections of the membrane result, wherein n is a natural number, and that, in each case, adjoining sections execute movements which are opposite in phase. In such case, n is larger than or equal to 1, i.e. n=1, 2, 3, 4, . . . . The sum of the sections is, especially, a whole numbered multiple of 2, i.e. the number of peaks and valleys, or the number of oscillatory regions of counterphase, in the oscillations is, in each case, equal.

An embodiment of the invention provides, that the driving/receiving unit and the membrane are embodied and matched to one another in such a manner, that the membrane executes mechanical oscillations, such that 2*n symmetric sections of the membrane result, wherein n is a natural number, and that, in each case, adjoining sections execute movements of counterphase. The case n=2 means, that the membrane has two transitions between sections of counterphase, and, thus, possesses two peaks and two valleys, which oscillate alternately relative to one another. The transition between such regions is a line, which extends through the middle of the membrane and along which no oscillations occur.

An embodiment of the invention includes, that a side of the membrane facing the medium is free of oscillatable units. Involved, thus, in this embodiment is a pure, membrane oscillator, whose membrane is free of a single-rod or of the fork tines of an oscillatory fork. Especially involved here is a counterphase, membrane oscillator. In other words: It involves a flush-mounting, membrane oscillator, which, because of the counterphase, membrane oscillations, is mechanically decoupled from the process connection.

An embodiment of the invention provides, that the driving/receiving unit and the membrane are embodied and matched to one another in such a manner, that the membrane, in the case, that the membrane is oscillating freely of the medium, executes mechanical oscillations with a frequency greater than 2 kHz. The first harmonic wave of the membrane lies, thus, above 2 kHz. The resonance frequency of an oscillatory fork lies, in comparison, for example, between 0.1 and 1.4 kHz. The frequency of the membrane oscillator depends, in such case, also on the dimensioning. With a greater diameter and a thinner membrane, also oscillations in the lower frequency range are possible.

An embodiment of the invention includes, that the driving/receiving unit and the membrane are embodied and matched to one another in such a manner, that the membrane, in the case, that the membrane is oscillating freely of the medium, executes mechanical oscillations with a frequency greater than 5 kHz.

An embodiment of the invention includes, that the driving/receiving unit and the membrane are embodied and matched to one another in such a manner, that the membrane, in the case, that the membrane is oscillating freely of the medium, executes mechanical oscillations with a frequency greater than 20 kHz. This concerns, for example, a membrane oscillator having a membrane of 1 inch diameter and 1 mm thickness.

An embodiment of the invention provides, that the membrane is circular or oval or rectangular or square.

An embodiment of the invention includes, that the membrane is secured by at least one mounting. In an embodiment, the mounting comprises a ring, to which the membrane is secured, and a screw-in piece, which adjoins the ring and which permits securement to the container, etc.

An embodiment of the invention provides, that at least one evaluation unit is provided, which evaluates the mechanical oscillations of the membrane as regards the process variable. The evaluation unit is, for example, a microcontroller, or, for example, an analog circuit, which detects and correspondingly evaluates change of frequency and/or amplitude in relation to a limit value.

An embodiment of the invention includes, that the evaluation unit evaluates the mechanical oscillations at least as regards whether the medium is at least partially covering the membrane. Especially for the process variable, fill level, the degree of covering of the membrane by the medium can be ascertained from the oscillations, i.e. from the characterizing variables, such as amplitude or frequency, of the oscillations of the membrane. However, also for other process variables, such as e.g. viscosity or density, a statement concerning the degree of covering is essential for ascertaining, or monitoring, the relevant process variable.

An embodiment of the invention provides that the driving/receiving unit includes at least one piezoelectric element.

An embodiment of the invention includes, that the piezoelectric element is embodied and/or contacted in such a manner, that the piezoelectric element has at least two separate regions, and that the piezoelectric element is arranged and connected with the membrane in such a manner, that the two separate regions of the piezoelectric element excite, each, a section of the membrane to execute mechanical oscillations. The piezoelectric element of the driving/receiving unit includes, thus, for example, two regions, which are polarized either in the same direction, e.g. axially, i.e. in the direction of the normals to the membrane, or in mutually opposite directions. Such a division can be produced, for example, by referencing the electrical contacting with electrodes correspondingly only to regions of the piezoelectric element. If the two regions of the piezoelectric element are supplied either with counterphase (equal polarization), or with equal phase (opposite polarization), alternating voltage signals, then each region executes a different oscillation, i.e. one region contracts (the thickness decreases) and the other region expands (the thickness increases). This leads to the fact that also the corresponding sections of the membrane, which, in each case, preferably, reside above different regions of the piezoelectric element, also, in each case, execute different oscillations. I.e., in this embodiment, located under a section of the membrane is a separate region of the piezoelectric element.

An embodiment of the invention provides, that a separating zone between the at least two separate regions of the piezoelectric element essentially is arranged in the vicinity of a separating zone between the sections of the membrane. In an embodiment, the piezoelectric element excites to oscillations of the mode, in which two sections of the membrane oscillate counterphasely relative to one another. For this, the piezoelectric element is contacted in such a manner, or it is embodied in such a manner, that two separate regions result in the piezoelectric region. The element is, in such case, arranged in such a manner relative to the membrane, that the separating zone between the two sections of the membrane is located above the separating region between the two separate regions of the piezoelectric element. The element is located, thus, in the case of a round membrane below a diagonal, or diameter, of the membrane, which extends between the two sections.

An embodiment of the invention includes, that the piezoelectric element is arranged and connected with the membrane in such a manner, that the piezoelectric element excites a section of the membrane to execute mechanical oscillations. In this embodiment, preferably, only one section of the membrane is excited to execute these oscillations.

An embodiment of the invention includes, that the driving/receiving unit has at least two piezoelectric elements, and that the piezoelectric elements are connected with the membrane at different regions. In this embodiment, thus, in each case, one piezoelectric element cares for the movement of one section of the membrane. The regions are to be selected suitably as a function of the type of oscillations to be excited.

An embodiment of the invention provides that the piezoelectric elements produce bending deformations of the membrane. Through the contacting with the membrane, which occurs, for example, via a full surface adhesion, thus, a bending oscillation is produced in the membrane, when the piezoelectric element is supplied with an alternating voltage. In an embodiment, the piezoelectric elements produce forces in the radial direction. Through the affixing of the elements to the membrane, the radial forces produce a corresponding deformation of the membrane.

The driving/receiving unit is composed, thus, in an embodiment, at least of two piezoelectric elements, which represent a so-called piezoelectric bimorph drive. The elements are, in such case, in an embodiment, adhered with the inner side of the membrane. Due to the adhesion, this is associated, on occasion, with a limitation of the temperature range.

An embodiment of the invention includes, that at least one blocking unit is provided, which is embodied and connected with the membrane in such a manner, that oscillations of the fundamental mode of the membrane are prevented by the blocking unit. In this embodiment, thus, oscillation of the membrane in the fundamental mode is prevented mechanically, in that such bending, for example, is prevented. Advantageous in this embodiment is that, in this way, a greater robustness is provided and a parasitic oscillation at a fundamental mode of the membrane is prevented.

In order to limit the degree of freedom of the membrane in the axial direction (first mode or fundamental wave), in the middle of the membrane, for example, a pin is secured as blocking unit. The pin is also fixed to the housing of the measuring device, e.g. to the mounting or to the screw-in piece holding the membrane. The size of the pin cross section is, in an embodiment, selected in such a manner, that, in the case of pressure loading of the membrane and, therewith, of the pin as blocking unit, the stresses in the cross section remain below the yield point. Additionally, the length of the pin is so selected, that the bending stiffness is large relative to the bending stiffness of the membrane. Due to this construction, the characteristics of the membrane determine, primarily, the oscillation frequency, and the blocking unit has only a subordinated influence on the oscillation frequency. Especially, the blocking unit is not a component of the resonator, which is excited to execute the oscillations and whose oscillations are taken into consideration for ascertaining and/or monitoring the process variable.

An embodiment of the invention provides that the blocking unit is secured on the side of the membrane facing away from the medium. The blocking unit is located, thus, on the inside, or in the inner space of the measuring device of the invention.

An embodiment of the invention includes, that the blocking unit is secured essentially in the middle of the membrane.

An embodiment of the invention provides, that the driving/receiving unit is embodied and connected with the blocking unit in such a manner, that the driving/receiving unit excites the membrane via the blocking unit to execute mechanical oscillations. The blocking unit fulfills, thus, in this embodiment, a triple function, in that it, on the one hand, prevents the fundamental oscillations and, on the other hand, produces the oscillations of the desired harmonic waves, as well as permitting an increased pressure loading on the membrane.

An embodiment of the invention includes, that the driving/receiving unit is connected mechanically with the blocking unit on the side facing away from the membrane. The driving/receiving unit is, thus, in this embodiment, placed, quasi, on the lower side of the blocking unit.

An embodiment of the invention provides that the driving/receiving unit produces essentially buckling movements.

An embodiment of the invention includes, that the driving/receiving unit is connected with the blocking unit mechanically, especially force interlockingly, along a symmetry axis of the blocking unit. In this embodiment, the driving/receiving unit is located on the side of the blocking unit.

An embodiment of the invention provides that the driving/receiving unit produces bending movements of the blocking unit along the symmetry axis.

The earlier described alternative embodiment of producing the oscillations has the advantage, that, then, the driving/receiving unit is farther from the process, from the medium and, therewith, from the temperatures and the process pressure reigning there, i.e. this embodiment can, thus, apply also in the case of higher temperatures, e.g. greater than 300° C. In this embodiment, through the blocking unit, which is embodied e.g. as a pin or as a rod, the counterphase, oscillatory mode of the membrane is directly excited. A further advantage is that also the process pressure loading allowable for the measuring device lies higher, than, for example, in the variant, wherein the piezoelectric elements of the driving/receiving unit are secured directly to the inner side of the membrane.

An embodiment includes, that at least one web is provided, that the web is mechanically coupled with the membrane, and that the driving/receiving unit is embodied and connected with the web in such a manner, that the web, at least at times, executes, essentially, a seesaw movement. In this embodiment, a web or a bridge is located, preferably, on the side of the membrane facing away from the medium. The web is, in such case, preferably, mechanically coupled with the membrane at two regions lying diametrally opposite to one another. The web is, in such case, excited by the driving/receiving unit to execute seesaw movements, wherein, for example, the two end regions of the web, through the driving/receiving unit, execute movements directed counter to one another, so that, as a whole, the movements of a seesaw, or rocker, result. I.e., if the one end region of the web moves away from the membrane, then the other end region is brought toward the membrane. Since the web, in an embodiment, is connected via two regions with the membrane, then also the membrane is excited at these two regions to counterphase movements. On the whole, thus, this embodiment of the exciting of oscillations can be referred to as a seesaw drive.

An embodiment provides that the web is mechanically coupled with the membrane via at least two support units. In an embodiment, there results, thus, as a whole, a U shaped unit formed of the two support units and the web, wherein the two ends of the U are connected with the membrane.

An embodiment includes, that the web and the two support units are embodied as one piece. In this embodiment, thus, for example, the web and the two support units form a single, U shaped component.

An embodiment provides that the blocking unit is arranged essentially in the middle of the web. This embodiment involves, thus, that the blocking unit is arranged essentially as a lengthening of the middle of the membrane. The blocking unit protrudes, thus, in an embodiment, through the middle of the web. In an additional embodiment, it terminates below the middle of the web. In an embodiment, the length of the web is essentially equal to the diameter of the circularly shaped membrane.

An embodiment includes, that the driving/receiving unit is arranged essentially in the middle of the web. If the driving/receiving unit is a piezoelectric element with two regions with polarization directed counter to one another, then, preferably, the separating zone between these two regions lies essentially in the middle of the web, wherein the two polarizations, in each case, are perpendicular to the web and one points away from the web and the other toward the web. Through this embodiment, one side of the web is pressed down, while the other side is drawn up. In such case, the orientations here are with reference to the inner side of the membrane, i.e. the side of the membrane facing away from the medium.

An embodiment provides, that the blocking unit penetrates the web or that the web penetrates the blocking unit, and that the driving/receiving unit is embodied to be ring-shaped, wherein the blocking unit protrudes through the annular driving/receiving unit or wherein the annular driving/receiving unit protrudes through the blocking unit. The web and the blocking unit are, thus, embodied and arranged in such a manner, that they mutually penetrate one another or are connected, or at least coupled, with one another.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
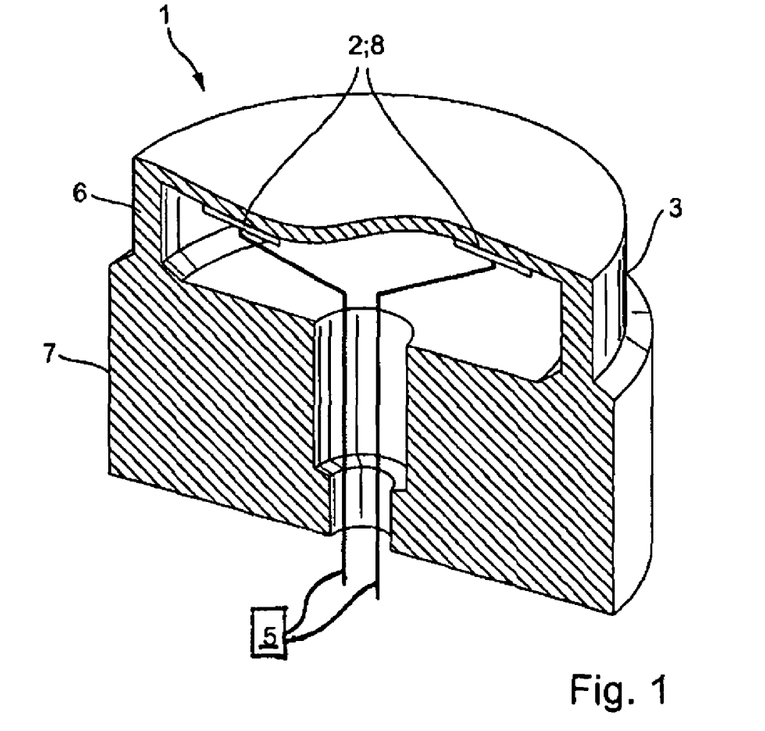
FIG. 1 a sectioned, three dimensional drawing of a first variant of the mechanical construction of a measuring device of the invention.

FIG. 1 shows the components directly participating in the oscillations of the measuring device of the invention. The mechanically oscillatable unit of the invention is composed only of the membrane 1. This has, for example, the advantage, that, then, the measuring device can be installed flushly mounted e.g. into, and with, the wall of a container, in which a medium is located. Serving for oscillation production here is the driving/receiving unit 2 composed of two piezoelectric elements 8, which are adhered securely to the inside surface of the membrane, i.e. on the side of the membrane facing away from the medium. This is a so-called bimorph drive. The elements are, in such case, polarized axially, i.e. perpendicularly to the membrane plane. If the elements of the driving/receiving unit 2 are supplied with an electrical, alternating voltage, then they expand in the direction of their polarization and contract in the radial direction. Through adhesion, this leads to the fact that the membrane 1, in each case, executes a bending deformation. If the two elements 2 are polarized oppositely to one another and they are supplied with the same voltage signal, or they have equal polarization, but are, however, excited counterphasely, then the membrane 1 executes, in one part, an oscillation upwardly, or outwardly, or in the direction of the medium and, in the other part, an oscillation in the direction of the interior of the measuring device. On the whole, thus, the membrane 1 is excited in its second eigenmode. An excitation of the first eigenmode, or the fundamental mode, is not possible, because of the arrangement of the two piezoelements 8. This is easy to see from FIG. 1. If other oscillation modes should be excited, then for such an excitement variant, a correspondingly higher number of piezoelectric elements should be used.

Conversely, the driving/receiving unit 2 also receives, in the illustrated example, mechanical oscillations and converts them into an electrical, alternating voltage. The characterizing variables of the oscillations, such as amplitude, frequency and phase as a function of frequency, relative to the exciting signal, depend on the degree of covering of the membrane 1 by the medium and also on some process variables of the medium, such as density, viscosity or attenuation. The evaluation of the received signal, and the determining, or monitoring, of the process variable therefrom, is performed by the evaluation unit 5. If the medium is, for example, a liquid, then a covering of the membrane 1 by the medium leads to a reduction of the oscillation frequency. In the case of bulk goods, the oscillation amplitude behaves correspondingly. Thus, the sinking of the frequency, or the amplitude, below a predeterminable, limit value can be interpreted to mean that the medium has reached, or exceeded, the fill level associated with the limit value. Conversely, a frequency, or amplitude, increase means that the desired fill level has been subceeded, or fallen beneath. The membrane 1 is, in such case, secured on the ring 6 of the mounting 3. The ring transitions into the screw-in piece 7, by means of which the measuring device is affixed to its location of application.

Figure 2:
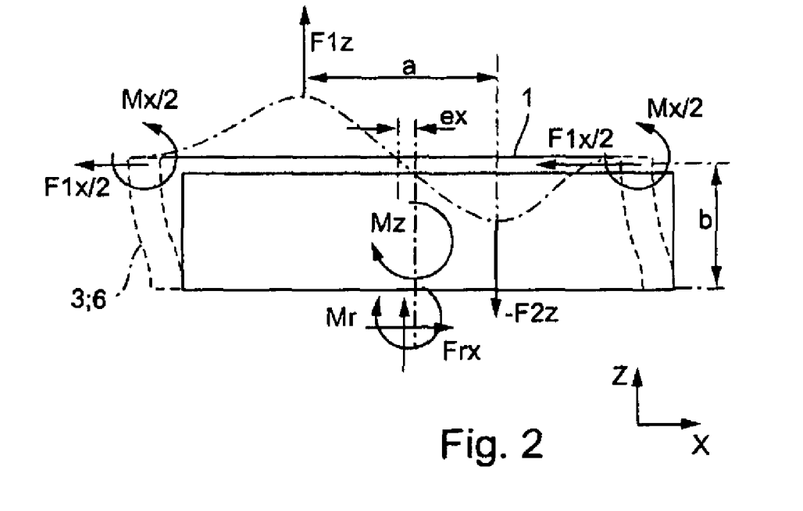
FIG. 2 a schematic drawing of the oscillatory movements of the membrane.

FIG. 2 shows a section through a schematic membrane 1 and its mounting 3, or ring 6. A not to scale depiction of the oscillatory movement is shown dashed and dotted. The membrane 1 executes, in such case, an oscillation of its second eigenmode. During the oscillatory movement of the membrane 1, the two membrane halves transmit in the X Z cutting plane illustrated in FIG. 2, based on the counterphase movement, forces F1z and −F1z, respectively, perpendicularly to the membrane plane, acting counterphasely. In the case of symmetric construction, the two acceleration forces are equal in direction and size and, so, cancel in the Z direction perpendicular to the membrane plane. Since the two forces are offset relative to one another by the distance a, they produce a torque $Mz(t)=F1z(t)*a$.

Due to the bending movement of the membrane 1, there are produced in the mounting 3 torques, which slightly deform the holding ring 6. The stiffnesses in the membrane mounting are, depending on movement direction, slightly different, e.g., the membrane shifting in the mounting is slightly larger, when it moves outwardly, or smaller, when it moves inwardly. This leads to the fact that the membrane 1, during the oscillatory movement, executes a small shifting ex in the radial direction and, thus, based on the moved mass, produces on both sides a force F1x/2. These forces act on the left and right sides in the same direction. The overall membrane movement in the radial direction corresponds to the offset ex. The torque $Mx(t)=F1x*b$ acts counter to the torque $Mz(t)$ in each phase of the oscillatory movement.

In the case of correct sizing of the moment arm b, then $Mx(t)=Mz(t)$, so that such an oscillatory system is per se decoupled. The reaction force Fr and the reaction moment Mr in the mounting are both zero. The membrane 1 thus serves alone for oscillation production, while a part of the mounting serves to absorb forces and moments.

The mounting 3 can be thought of here as the elastic holding ring 6, which is affixed at its lower region to the solid, screw-in piece 7.

Figure 3:
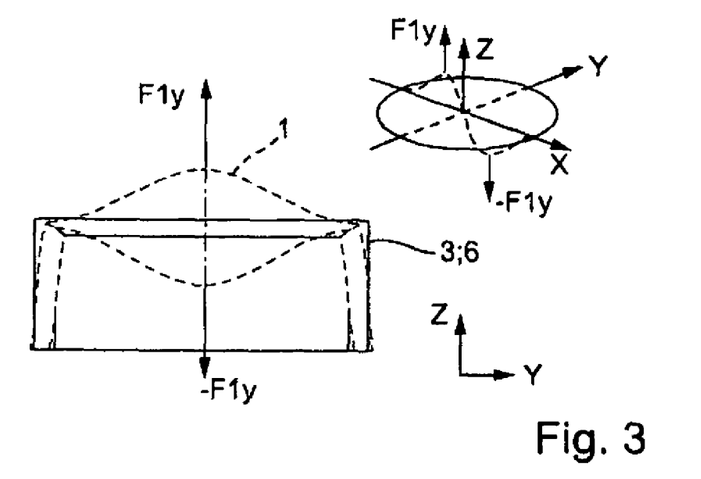
FIG. 3 another section through the membrane of FIG. 2.

FIG. 3 shows another section through the membrane 1 and the mounting 3, or its upper ring 6. Two oscillation directions are presented in the form of dashed lines. The plane perpendicular to the oscillation direction is force and torque free in the radial direction, because the almost movement free "neutral line" (indicated along the Y axis) in the plane of oscillation experiences in the reversal of the membrane 1, in the ideal case, no deformation.

Figure 4:
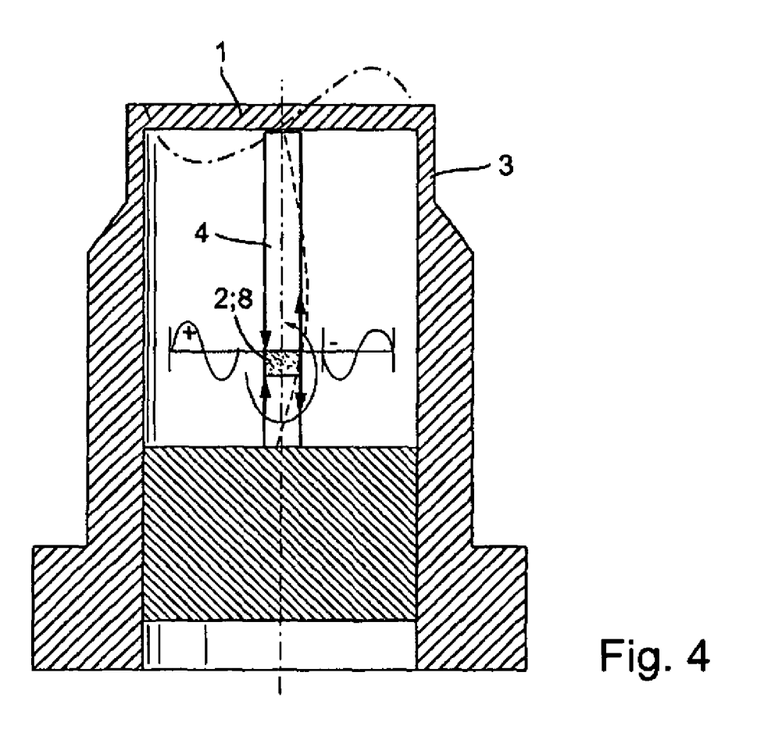
FIG. 4 a section through the mechanical construction of a second variant.

The membrane oscillator shown in FIG. 4 is equipped with a rod as blocking unit 4, which fixedly connects the membrane 1 with the screw-in piece 7 of the mounting 3. The rod 4 need, however, not be connected directly with the screw-in piece 7. For the functioning of the blocking of the fundamental oscillations, alone at least one affixing must be provided. Interposed in the rod 4 at the lower end is a piezoelectric ring element 8 as driving/receiving unit 2, with which the membrane 1 is excited.

For the oscillation excitement, the piezoelectric element 8 possesses two electrodes electrically isolated from one another. If, on the first electrode, an alternating voltage is applied, and, on the second electrode, an equally large, however, counterphase, alternating voltage, then the rod 4, based on the axially asymmetric deformation of the piezoelement 2, executes bending oscillations. The back and forth movement of the rod 4 transmits to the membrane 1 an alternating torque. The oscillation frequency corresponds, in such case, to the eigenfrequency of the counterphase, membrane mode.

Through the compelled movement of the rod 4, the first eigenmode, or the fundamental mode, existing in the oscillator cannot be excited, which is advantageous for the complete oscillatory system, including the feedback electronics (not shown), with which the driving/receiving unit 2 is connected.

While the bimorph drive of FIG. 1 can be designed to function up to a maximum 150° C., the rod drive can be applied at more than 300° C. The application limit is not governed by the oscillator material, but, instead, by the applied piezoelectric material. As regards the process pressure loading, the rod 4 offers, relative to the bimorph embodiment, an additional advantage, because it stabilizes the membrane 1 and, thus, higher pressure loadings can be borne.

If one considers the oscillatory mode (dashed line) shown in FIG. 4, then one detects a position, in which, based on the counterphase movement of the membrane 1, no, or only very low, movements are present. More precisely, it is a point in the membrane middle, or a line transverse to the symmetry axis, which is almost movement free. If one secures, in the immediate vicinity of the membrane middle, a rod 4, then the fundamental mode of the free membrane exists no longer, because the degree of freedom in the axial Z direction is constrained by the rod, i.e. the fundamental mode is blocked. As a result, the first eigenmode present in the oscillator is the counterphase, membrane movement, thus the first harmonic wave of the membrane 1, which offers advantages as regards the electronics design. An additional advantage is to be seen in the pressure range. The rod offers an increased stability for the membrane 1 standing under process pressure. The maximum achievable process pressure for a sensor with a ¾ inch large membrane 1 with a thickness of 0.8 mm lies in the order of magnitude of 100 bar, without that plastic deformations are to be feared. Advantageously, furthermore, is that the rod 4 can be used directly as drive. In this regard, an axially polarized piezoelectric element 8 with unilaterally separated electrodes (right and left of the symmetry axis) is interposed in the rod 4. In the case of applying an electrical, alternating voltage to one electrode and counterphase to the other electrode (shown by the two signal curves of the applied alternating voltage signals), the piezoelement 2 transmits, transversely to the symmetry axis, a time-dependent torque onto the rod 4. This torque is transferred via the elastic connection directly to the membrane 1. The excitation frequency of the counterphase, oscillatory mode of the membrane 1 corresponds, in such case, to the counterphase, bending mode of the membrane 1.

The equal phase mode, in the case of which the complete membrane 1 is moved in equal direction in a fundamental wave oscillation, cannot be activated by the drive 2.

Figure 5:
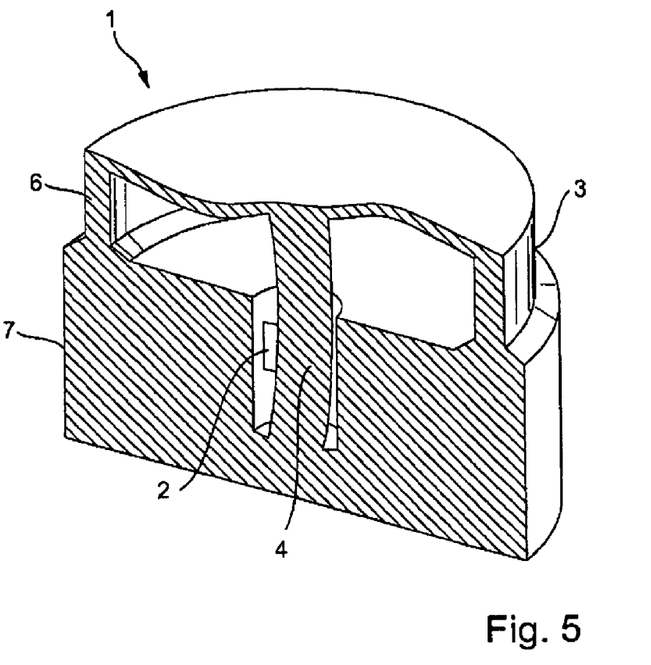
FIG. 5 a sectioned, three dimensional drawing of the second variant of the mechanical construction of FIG. 4.

FIG. 5 shows another variant of the oscillation production, in which the driving/receiving unit 2 is placed on the side of the blocking unit 4. The membrane 1 is, in this case, shown oscillating. Here, likewise, bending movements are produced, which excite the rod 4 to execute buckling movements. This oscillation production can also be produced by coil arrangements on the blocking unit 4. In the drawing, also the upper part of the mounting 3 can be seen in the form of a ring 6, which with the foundational body 7 is securely connected.

Figure 6A:
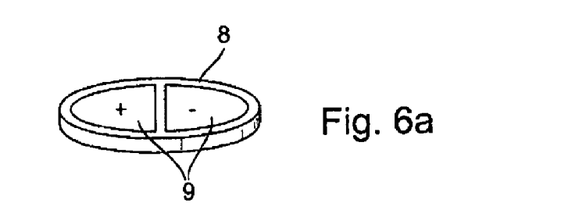
FIGS. 6a, b and c three schematic representations of a piezoelectric element for application in a measuring device of the invention.

FIG. 6a shows a piezoelectric element 8, such as can be applied, for example, in a driving/receiving unit. The element 8 is disc shaped with round or oval surface, with which it is also, preferably, secured to the membrane. The polarization extends, in such case, preferably, in the axial direction, i.e., in the installed state, perpendicular to the membrane plane. In this embodiment, in such case, the polarizations of the two regions 9 of the element 8 are opposite to one another. This is indicated by the plus and minus signs.

Figure 6B:
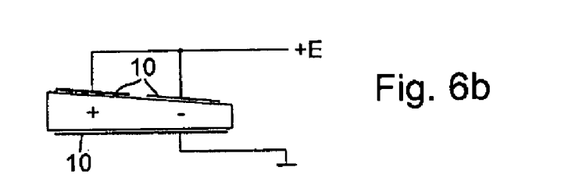
Figure 6C:
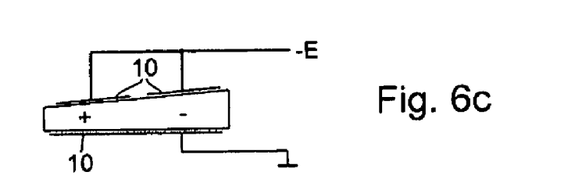

In FIGS. 6b and 6c, the case is presented, wherein, via the electrodes 10, the piezoelectric element 8 is supplied with an alternating voltage (state with +E in FIG. 6b and with −E in FIG. 6c). Here, all parts of the lower surface of the element 8 are connected with ground. Depending on the applied voltage, a region 9 contracts, or expands, so that an alternating voltage also produces a corresponding oscillation of the thickness of the piezoelectric element 8. The advantage of this is that a single piezoelectric element 8 produces, quasi, two sub-movements. Through suitable connection with the membrane, also, in each case, a section of the membrane—in each case, as a function of above which region of the piezoelectric element 8 the section is located—executes its own oscillation, wherein, moreover, the oscillations of the sections located above the regions of the piezoelectric element are counterphase oscillations. Furthermore, this piezoelectric element 8 does not permit excitation of a fundamental mode of the membrane.

In order that the sections, in each case, experience equal force, or that also the sensitivity for the oscillations in the detection is, likewise, in each case, equally large, the separate regions 9 of the piezoelectric element 1 have, in each case, essentially the same size.

Figure 7A:
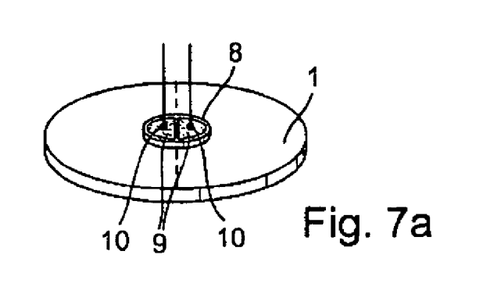
FIGS. 7a, b and c three variants for the contacting of a piezoelectric element in connection with the membrane, and FIG. 8 a sectioned, three dimensional drawing of a third variant of the mechanical construction.
Figure 7B:
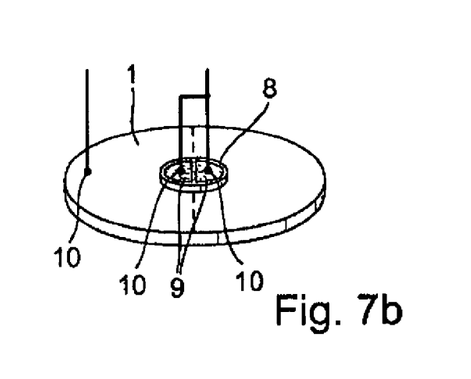
Figure 7C:
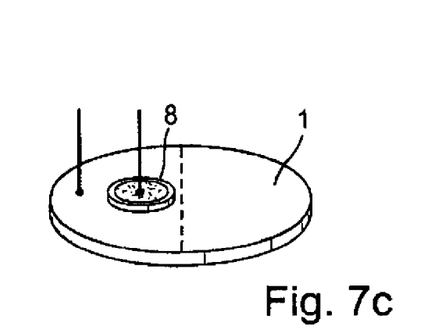

Shown in FIG. 7, by way of example, are three variants for the embodiment of driving/receiving unit 2, or the piezoelectric element 8, and membrane 1.

FIG. 7a shows a piezoelectric element 8, which is secured to the inner side of the membrane 1. The membrane 1 should here be excited to such oscillations, in the case of which two symmetric sections oscillate counterphase relative to one another. Thus, quasi, the first harmonic wave is excited. The membrane 1 should be, in such case, be circular, so that the two sections have, in each case, a semicircular form. The membrane 1 is, in such case, —here not shown—connected at its edge force-interlockingly with the process connection.

The piezoelectric element 8 is axially polarized, i.e. the polarization extends perpendicular to the membrane plane. Applied on the piezoelectric element 8 are two symmetric electrodes 10. For the oscillation production, counterphase signals are sent to the electrodes 10. If it is, especially, an electrical, alternating voltage signal, then the regions 9 of the piezoelectric element 8 execute, in each case, counterphase, thickness oscillations, i.e. one region contracts, while the other expands.

Especially, here, the separating zone between the two regions of the piezoelectric element 8 is placed on top of the separating zone, or the dividing line, of the membrane 1, so that, thus, a region of the piezoelectric element 8 is right above (or, as seen from the process side, below) a section of the membrane 1. I.e., the, in this case, round piezoelectric element 8 is arranged in the middle of the, in this case, round membrane 1. The piezoelectric element 8 is, in such case, for example, a ceramic, or, in another embodiment, a single crystal.

In FIG. 7*b*, the two electrodes 10 are electrically short circuited. In such case, the—here, especially, electrically conductively embodied—membrane 1 is connected with an additional electrode. Applied to the electrodes 10 of the piezoelectric element 8, or to that of the membrane 1, is an alternating voltage, so that the oscillations are produced.

FIG. 7*c* shows another embodiment, in the case of which the piezoelectric element 8 is applied below one section of the membrane 1. The piezoelectric element 8 serves here completely for the oscillation production of the corresponding section. Applied to the electrodes of the membrane 1 and the piezoelectric element 8, respectively, is, also here, an alternating voltage signal. The net result therefrom is that the two symmetric, i.e. equally large, sections of the membrane 1 oscillate counterphasely.

In the measuring device of the invention, thus, the harmonic waves of the membrane, which are composed of the counterphase oscillations of sections of the membrane, are taken into consideration for determining and/or monitoring the process variable. Alternatively, it can be formulated, that the membrane is excited to oscillation modes, which lie above the fundamental mode or the mode with the lowest eigenfrequency, and that these modes are distinguished by the fact that sections of the membrane, which are symmetric relative to one another, execute counterphase oscillations. The measurements start, in such case, from the interaction between membrane 1 and medium, or from the effects of the medium on the characterizing variables of the mechanical oscillations. The harmonic waves are, in such case, for example, produced in such a manner, that the driving/receiving unit can produce only harmonic waves or that the fundamental wave of the membrane is suitably suppressed.

Figure 8:
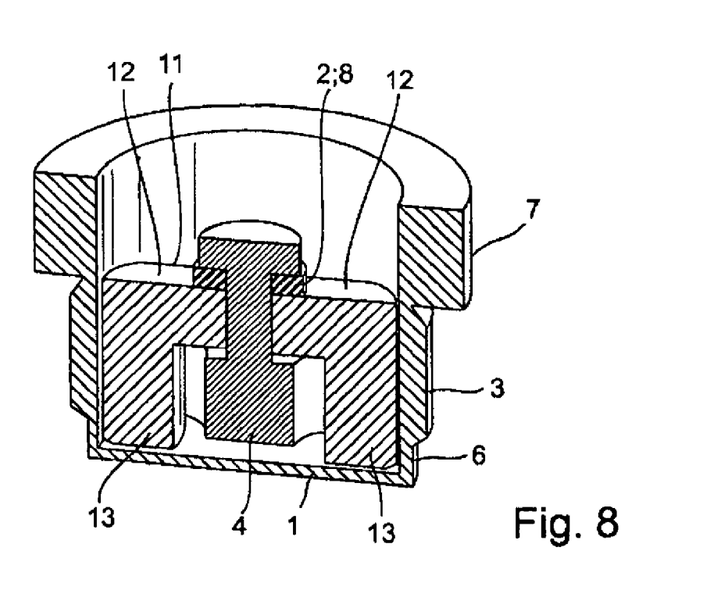

FIG. 8 shows another embodiment of the membrane oscillator in section. This is a kind of seesaw drive. Behind the membrane 1, i.e. located on the side facing away from the medium, is located a seesaw, or rocker, which is formed by a web 11, which is here arranged essentially parallel to the area of the membrane 1, and two support units 13. Via the support units 13, thus, the web 11 is mechanically coupled with the membrane 1. In the case illustrated here, the seesaw, or rocker, is embodied as one-piece in the form of a U. In the case of the, here, circularly shaped membrane 1, the web 11 equals a widened diagonal, or diameter, of a circle parallel to the membrane 1.

Arranged above the middle of the membrane 1 is the blocking unit 4, which passes through the middle of the web 11. Blocking unit 4 and web 11 thus fit sectionally into one another. Clamped between a flange on the end of the blocking unit 4 and the web 11 is the driving/receiving unit 2, which is embodied here as piezoelectric element 8. Along the axis of the circularly shaped piezoelectric element 8, the blocking unit 4 passes through the piezoelectric element 8. The piezoelectric element 8 includes—such as above described in detail—two regions, which are polarized oppositely to one another. If a voltage is applied to this element 8, then one side of the web 11 is moved toward the membrane 1 and the other side away. I.e., especially, the end regions 12 of the web exhibit counterphase movements. Through an alternating voltage, a seesaw movement of the web 11, thus, results.

The two support units 13 rest, in such case, only at their outermost locations on the membrane 1, so that the mechanical properties of the membrane 1 are scarcely influenced.

The invention claimed is:

1. An apparatus for determining and/or monitoring at least one process variable of a medium, comprising:
    at least one mechanically oscillatable membrane, which has a plurality of natural eigenmodes; and
    at least one driving/receiving unit, which excites the membrane to execute mechanical oscillations and/or which receives mechanical oscillations from said membrane, wherein:
    said driving/receiving unit and said membrane are embodied and matched to one another in such a manner, that said membrane only executes mechanical oscillations, which correspond to modes, which lie above the fundamental mode of said membrane; and
    a side of said membrane facing the medium is free of oscillatable units.

2. The apparatus as claimed in claim 1, wherein:
    said driving/receiving unit and said membrane are embodied and/or arranged relative to one another in such a manner, that the occurrence of mechanical oscillations of said membrane, which correspond to the fundamental mode of said membrane, are essentially prevented.

3. The apparatus as claimed in claim 1, wherein:
    said driving/receiving unit excites essentially only said membrane to execute oscillations.

4. The apparatus as claimed in claim 1, wherein:
    said driving/receiving unit and said membrane are embodied and matched to one another in such a manner, that said membrane executes such mechanical oscillations, that $2*n$ sections of said membrane result, and that, in each case, adjoining sections execute movements of counterphase, wherein n is a natural number.

5. The apparatus as claimed in claim 1, wherein:
    said driving/receiving unit and said membrane are embodied and matched to one another in such a manner, that said membrane executes such mechanical oscillations, that $2*n$ symmetric sections of said membrane result, and that, in each case, adjoining sections execute movements of counterphase, wherein n is a natural number.

6. The apparatus as claimed in claim 1, wherein:
    said driving/receiving unit and said membrane are embodied and matched to one another in such a manner, that said membrane, when oscillating free of medium, executes mechanical oscillations with a frequency greater than 2 kHz.

7. The apparatus as claimed in claim 6, wherein:
    said driving/receiving unit and said membrane are embodied and matched to one another in such a manner, that said membrane, when oscillating free of medium, executes mechanical oscillations with a frequency greater than 5 kHz.

8. The apparatus as claimed in claim 7, wherein:
    said driving/receiving unit and said membrane are embodied and matched to one another in such a manner, that said membrane, when oscillating free of medium, executes mechanical oscillations with a frequency greater than 20 kHz.

9. The apparatus as claimed in claim 1, wherein:
    said membrane is embodied to be circular or oval or rectangular or square.

10. The apparatus as claimed in claim 1, wherein:
    said membrane is secured by at least one mounting.

11. The apparatus as claimed in claim 1, further comprising:

at least one evaluation unit, which evaluates the mechanical oscillations of said membrane as regards the process variable.

12. The apparatus as claimed in claim 11, wherein:
said evaluation unit evaluates the mechanical oscillations at least as regards whether medium at least partially covers said membrane.

13. The apparatus as claimed in claim 1, wherein:
said driving/receiving unit has at least one piezoelectric element.

14. The apparatus as claimed in claim 13, wherein:
said piezoelectric element is embodied and/or contacted in such a manner, that said piezoelectric element has at least two separate regions, and said piezoelectric element is arranged and connected with said membrane in such a manner, that the two separate regions of said piezoelectric element, in each case, excite a section of said membrane to execute mechanical oscillations.

15. The apparatus as claimed in claim 14, wherein:
a separating zone between said at least two separate regions of said piezoelectric element is arranged essentially in the vicinity of a separating zone between the sections of said membrane.

16. The apparatus as claimed in claim 13, wherein:
said piezoelectric element is arranged and connected with said membrane in such a manner, that said piezoelectric element excites a section of said membrane to execute mechanical oscillations.

17. The apparatus as claimed in claim 13, wherein:
said driving/receiving unit has at least two piezoelectric elements, and said piezoelectric elements are connected at different regions with said membrane.

18. The apparatus as claimed in claim 17, wherein:
said piezoelectric elements produce bending deformations of said membrane.

19. The apparatus as claimed in claim 1, further comprising:
at least one blocking unit, which is embodied and connected with said membrane in such a manner, that oscillations of the fundamental mode of said membrane are prevented by said blocking unit.

20. The apparatus as claimed in claim 19, said blocking unit is secured to the side of said membrane facing away from the medium.

21. The apparatus as claimed in claim 20, wherein:
said blocking unit is secured essentially in the middle of said membrane.

22. The apparatus as claimed in claim 19, wherein:
said driving/receiving unit is embodied and connected with said blocking unit in such a manner, that said driving/receiving unit excites said membrane via said blocking unit to execute mechanical oscillations.

23. The apparatus as claimed in claim 22, wherein:
said driving/receiving unit is mechanically connected with said blocking unit on the side facing away from said membrane.

24. The apparatus as claimed in claim 23, wherein:
said driving/receiving unit produces essentially buckling movements.

25. The apparatus as claimed in claim 22, wherein:
said driving/receiving unit is connected mechanically, especially force interlockingly, with said blocking unit along a symmetry axis of said blocking unit.

26. The apparatus as claimed in claim 25, wherein:
said driving/receiving unit produces bending movements of said blocking unit along the symmetry axis.

27. The apparatus as claimed in claim 1, further comprising:
at least one web, which is mechanically coupled with said membrane, wherein:
said driving/receiving unit is embodied and connected with said web in such a manner, that said web executes, at least at times, essentially a seesaw movement.

28. The apparatus as claimed in claim 27, wherein:
said web is mechanically coupled with said membrane via at least two support units.

29. The apparatus as claimed in claim 28, wherein:
said web and said two support units are embodied as one piece.

30. The apparatus as claimed in claim 27, wherein:
said blocking unit is arranged essentially in the middle of said web.

31. The apparatus as claimed in claim 27, wherein:
said driving/receiving unit is arranged essentially in the middle of said web.

32. The apparatus as claimed in claim 27, wherein:
said blocking unit penetrates said web or said web penetrates said blocking unit; and
said driving/receiving unit is ring-shaped, wherein said blocking unit protrudes through said annular driving/receiving unit or wherein said annular driving/receiving unit protrudes through said blocking unit.

* * * * *